United States Patent
Lee et al.

(10) Patent No.: US 8,202,434 B2
(45) Date of Patent: Jun. 19, 2012

(54) METHOD OF MANUFACTURING HOLLOW MICRONEEDLE STRUCTURES

(75) Inventors: Dae Sik Lee, Daejeon (KR); Hyun Woo Song, Daejeon (KR); Moon Youn Jung, Daejeon (KR); Seon Hee Park, Daejeon (KR)

(73) Assignee: Electronics and Telecommunications Research, Daejeon (KR)

( * ) Notice: Subject to any disclaimer, the term of this patent is extended or adjusted under 35 U.S.C. 154(b) by 427 days.

(21) Appl. No.: 12/621,594

(22) Filed: Nov. 19, 2009

(65) Prior Publication Data

US 2011/0011827 A1 Jan. 20, 2011

(30) Foreign Application Priority Data

Jul. 17, 2009 (KR) .................... 10-2009-0065324

(51) Int. Cl.
*B44C 1/22* (2006.01)
(52) U.S. Cl. ............... 216/11; 216/22; 216/37; 604/46; 604/272; 426/106
(58) Field of Classification Search .............. 216/11, 216/22, 37; 604/46, 272; 426/106
See application file for complete search history.

(56) References Cited

U.S. PATENT DOCUMENTS

| | | | |
|---|---|---|---|
| 6,334,856 B1 * | 1/2002 | Allen et al. | 604/191 |
| 7,332,197 B2 | 2/2008 | Wood et al. | |
| 2002/0138049 A1 | 9/2002 | Allen et al. | |
| 2004/0146611 A1 | 7/2004 | Arias et al. | |
| 2006/0025717 A1 | 2/2006 | Zimmermann et al. | |
| 2006/0226016 A1 | 10/2006 | S/O Govinda Raju et al. | |

FOREIGN PATENT DOCUMENTS

| | | |
|---|---|---|
| KR | 1020040074167 A | 8/2004 |
| WO | 2005/049107 A2 | 6/2005 |

OTHER PUBLICATIONS

Patrick Griss, et al; "Side-Opened Out-of-Plane Microneedles for Microfluidic Transdermal Liquid Transfer", Journal of Microelectromechanical Systems, vol. 12, No. 3, pp. 296-301, Jun. 2003 (Exact date not given).

* cited by examiner

*Primary Examiner* — Nadine Norton
*Assistant Examiner* — Maki Angadi
(74) *Attorney, Agent, or Firm* — Ladas & Parry LLP

(57) ABSTRACT

Provided is a method of manufacturing a hollow microneedle structure. The method includes forming an injection mold having a through hole, filling the injection mold with a photoresist formed of a viscous material, and extruding the photoresist from the injection mold through the through hole, solidifying the extruded photoresist to form a needle-type photoresist structure, forming a seed layer on the surface of the photoresist structure, forming a metal plated layer on the seed layer, inclining an end tip of the photoresist structure having the metal plated layer, and removing the photoresist from the metal plated layer to form a hollow. Thus, the hollow microneedle structure can be manufactured to have such diameter, length, hardness, and inclination angle as to minimize pain. The hollow microneedle structure can be combined with an apparatus for detecting a biomaterial or injecting cosmetic substances or medicines, and variously applied.

9 Claims, 10 Drawing Sheets

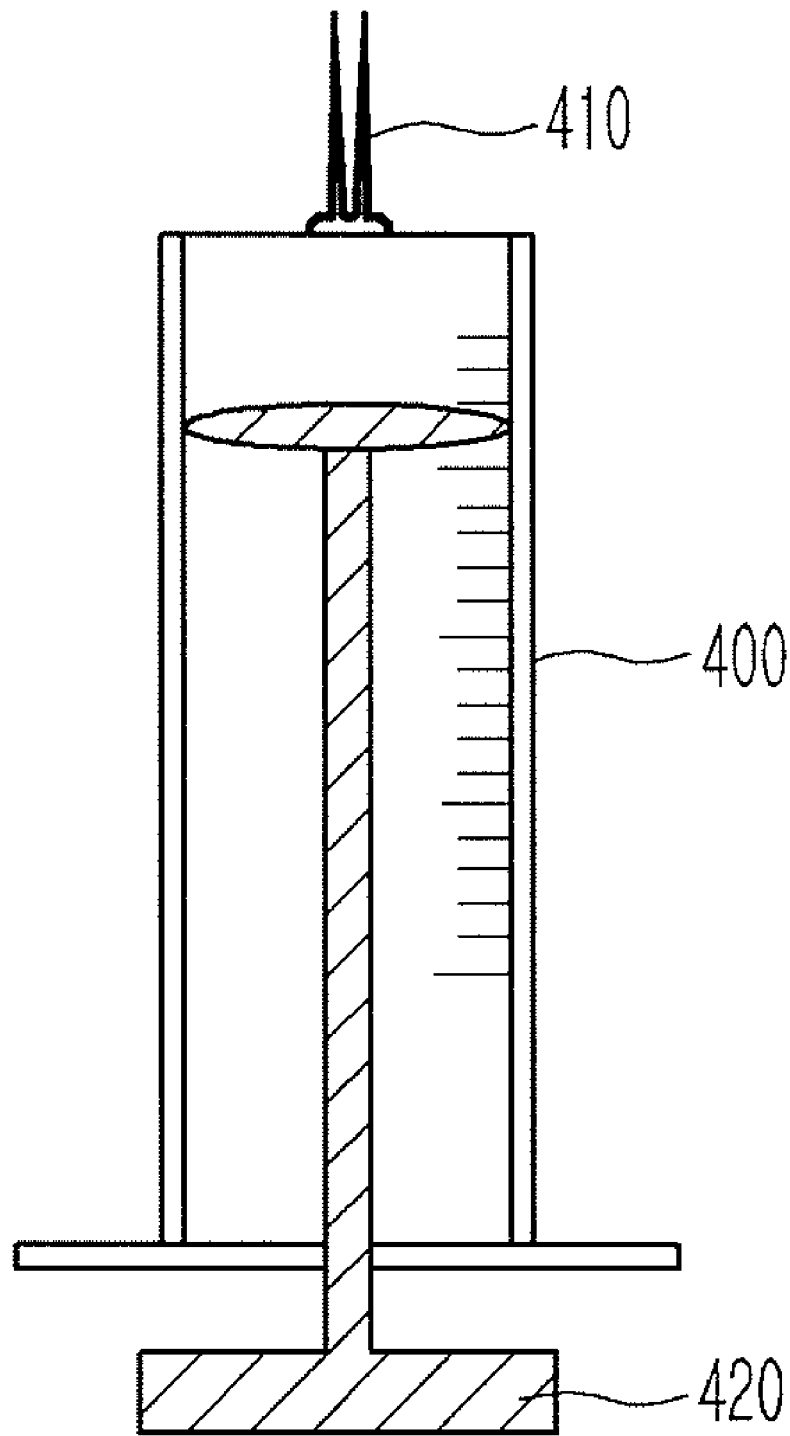

METHOD OF MANUFACTURING HOLLOW MICRONEEDLE STRUCTURES

CROSS-REFERENCE TO RELATED APPLICATION

This application claims priority to and the benefit of Korean Patent Application No. 10-2009-0065324, filed Jul. 17, 2009, the disclosure of which is incorporated herein by reference in its entirety.

BACKGROUND

1. Field of the Invention

The present invention relates to a method of manufacturing microneedles, and more specifically, to a method of manufacturing hollow microneedles having inclined end tips.

2. Discussion of Related Art

In the field of bio-microelectromechanical systems (bio-MEMS) technology, samples may need to be pretreated in order to enable early detection and chemical analysis for diseases on small chips. This requires collecting blood while minimizing pain. Accordingly, an essential component called a microneedle is required.

In general, needles are variously utilized in hospitals. For example, the needles are used to collect biomaterials, such as blood, in order to detect diseases, inject drugs into the living body, or perform cosmetic treatment of the skin.

A vast amount of research has been conducted on developing various applicable bioanalysis chips all over the world.

However, conventional needles used to collect biomaterials, such as blood, are practically problematic because they may cause pain during use and inflict external injuries.

Therefore, the demand for new microneedles capable of collecting blood while minimizing pain has increased globally.

Conventionally, probe-type microspikes, solid microneedles, and hollow microneedles have been proposed.

Compared to conventional needles, microneedles are capable of minimizing pain during penetration into the skin without leaving external injuries.

In order to minimize pain while penetrating the skin, a top diameter of a needle is important in providing more opportunities to avoid pain spots on the skin. Above all, a microneedle should penetrate a stratum corneum and a epidermis having a thickness of about 10 to 20 $\mu m$ and 100 $\mu m$, respectively. To do this, the microneedle needs to have a certain degree of physical strength.

In addition, a microneedle should have an appropriate length as to reach as far as a capillary vessel in order to effectively collect blood or transmit medicine.

In consideration of all the above-described points, a technique of manufacturing a solid silicon microneedle having an out-of-plane shape using silicon MEMS technology has been introduced. However, this technique requires an additional etching process to provide a hollow needle shape, or does not satisfy a required needle length.

Meanwhile, although a microneedle having a sufficient length has recently been proposed using a drawing method, the proposed microneedle neither ensures verticality and uniformity nor realizes process simplification.

SUMMARY OF THE INVENTION

The present invention is directed to a method of manufacturing a hollow microneedle structure, which can ensure such a hardness as to penetrate the skin and such a length as to reach a capillary vessel. Also, the method of manufacturing the hollow microneedle structure may provide a microneedle structure having vertical and uniform needles and simply formed hollows.

One aspect of the present invention provides a method of manufacturing a microneedle structure. The method includes: forming an injection mold having a through hole; filling the injection mold with a photoresist formed of a viscous material, and extruding the photoresist from the injection mold through the through hole; solidifying the extruded photoresist to form a needle-type photoresist structure; forming a seed layer on the surface of the photoresist structure; forming a metal plated layer on the seed layer; inclining an end tip of the photoresist structure having the metal plated layer; and removing the photoresist from the metal plated layer to form a hollow.

The method may further include bringing a subsidiary substrate into contact with the extruded photoresist such that the photoresist has a pillar-type needle shape.

The microneedle structure may have an outer diameter of about 40 to 200 $\mu m$ and an inner diameter of about 10 to 150 $\mu m$.

The microneedle structure may have an effective length of about 0.5 to 5 mm.

The formation of the injection mold having the through hole may include: forming a photoresist layer on a substrate; exposing and developing the photoresist layer to form a mask; forming a predetermined number of through holes in the substrate according to the type of the mask; and assembling the substrate to form a bottom surface of the injection mold.

The inclination of the end tip of the photoresist structure having the metal plated layer may include: coating the metal plated layer with a slurry; cutting the metal plated layer at a predetermined inclination angle to increase an effective sectional area; and removing the slurry.

The slurry may be removed during the removal of the photoresist from the metal plated layer.

The inclination angle may range from about 20 to 80 degrees.

The method may further include chemically treating the through hole to prevent the hardening of a biomaterial.

BRIEF DESCRIPTION OF THE DRAWINGS

The above and other features and advantages of the present invention will become more apparent to those of ordinary skill in the art by describing in detail exemplary embodiments thereof with reference to the attached drawings in which:

FIG. 6 is a construction diagram of an application example of the microneedle structure of FIG. 1.

DETAILED DESCRIPTION OF EMBODIMENTS

Figure 1:
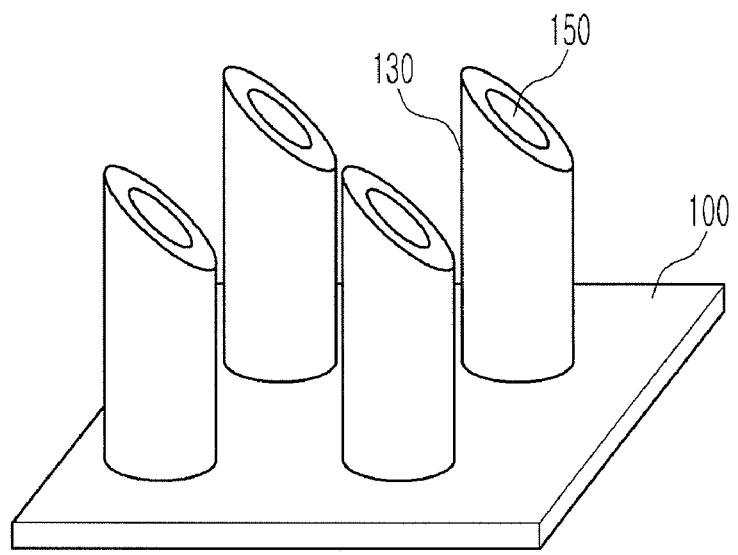
FIG. 1 is a construction diagram of a microneedle structure according to an exemplary embodiment of the present invention.

The present invention will be described more fully hereinafter with reference to the accompanying drawings, in which exemplary embodiments of the invention are shown. This invention may, however, be embodied in many different forms and should not be construed as being limited to the embodiments set forth herein. Rather, these embodiments are provided so that this disclosure is thorough and complete and fully conveys the concept of the invention to those skilled in the art. In the drawings, portions irrelevant to a description of the invention are omitted for brevity, and like numbers refer to like elements throughout.

Hereinafter, a microneedle structure according to an exemplary embodiment of the present invention will be described with reference to FIG. 1.

Referring to FIG. 1, a microneedle structure manufactured according to an exemplary embodiment of the present invention may include a plurality of cylindrical microneedles 130. Each of the cylindrical microneedles 130 may include a hollow 150 formed in the center thereof.

That is, the plurality of microneedles 130 may be vertically formed on a single substrate 100, and an end tip of each of the microneedles 130 may be inclined.

Each of the microneedles 130, which may be obtained by plating a metal seed with nickel, may have a hollow 150 with a very small diameter of, for example, 20-150 μm or less, and satisfy an outer diameter of about 40 to 200 μm, an inner diameter of about 10 to 150 μm, and an effective length of about 0.5 to 5 mm.

The microneedles 130 may be formed by injecting photoresist into the substrate 100 having fine through holes that are formed using microelectromechanical systems (MEMS) technology.

Hereinafter, a method of manufacturing the microneedle structure of FIG. 1 will be described with reference to FIGS. 2A through 4B.

Figure 2A:
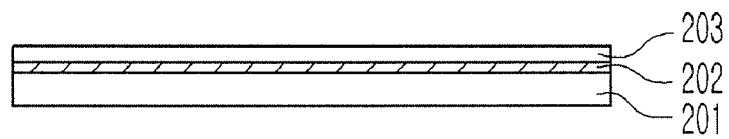
FIGS. 2A through 2M are cross-sectional views illustrating a method of manufacturing the microneedle structure of FIG. 1.
Figure 2B:
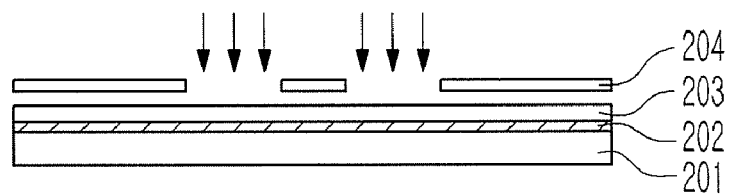
Figure 2C:
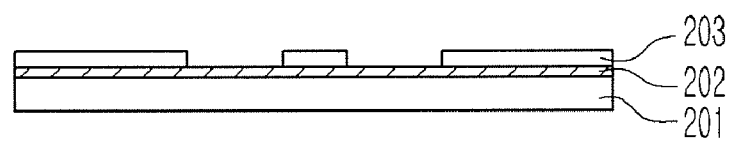
Figure 2D:
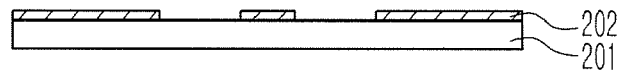
Figure 2E:
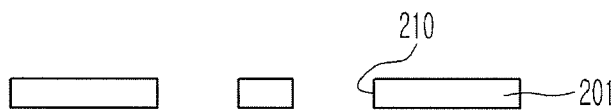
Figure 2F:
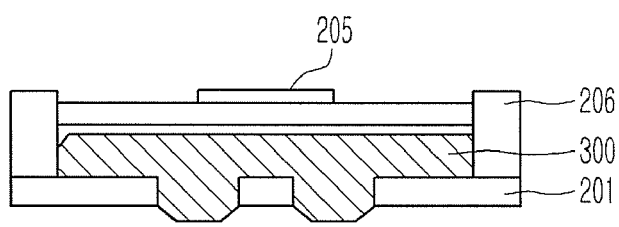
Figure 2G:
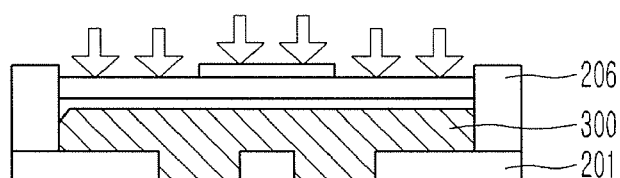
Figure 2G:
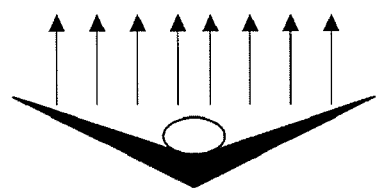
Figure 2H:
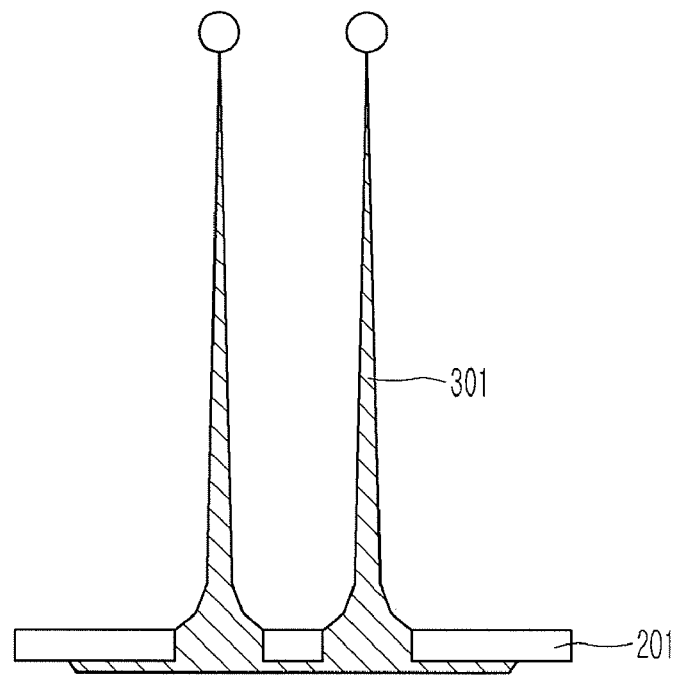
Figure 2I:
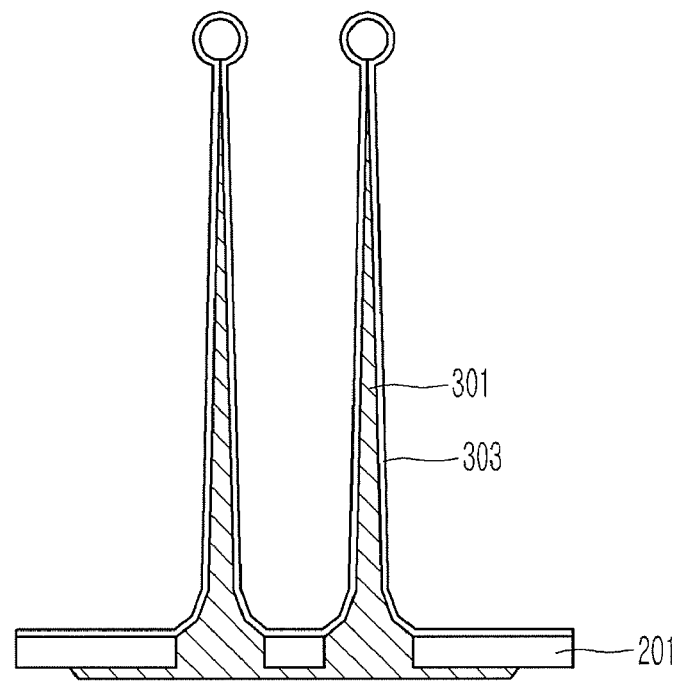
Figure 2J:
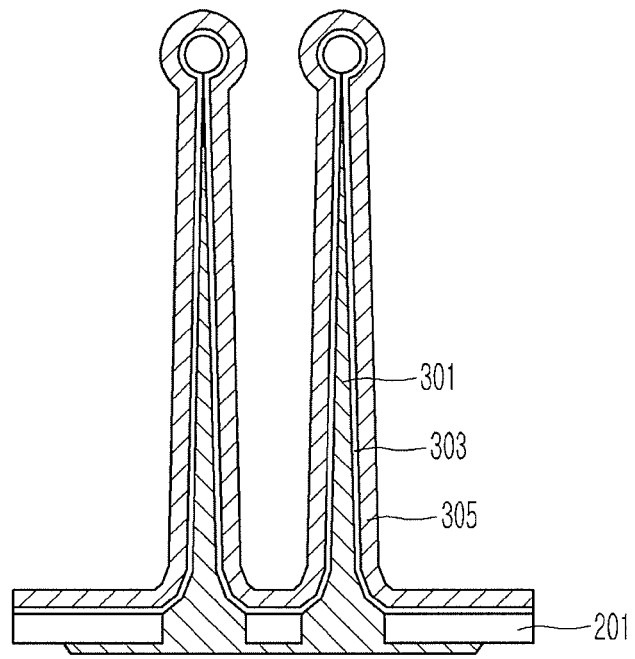
Figure 2K:
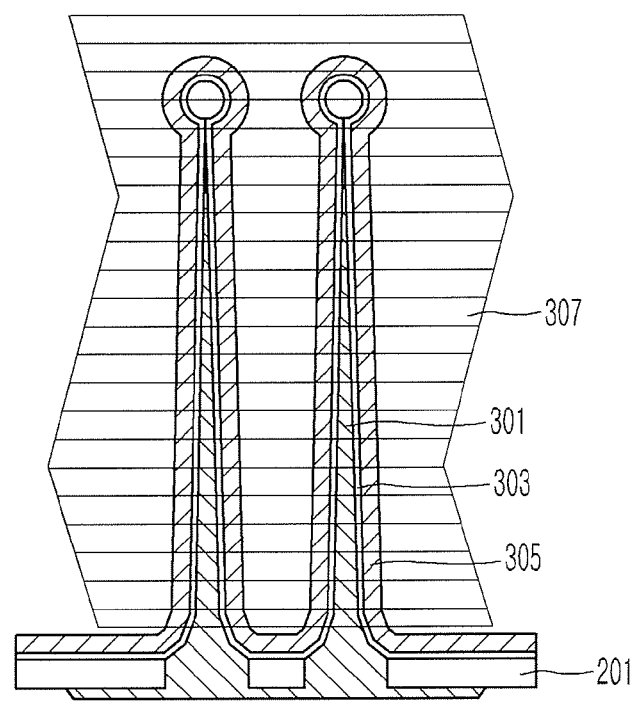
Figure 2L:
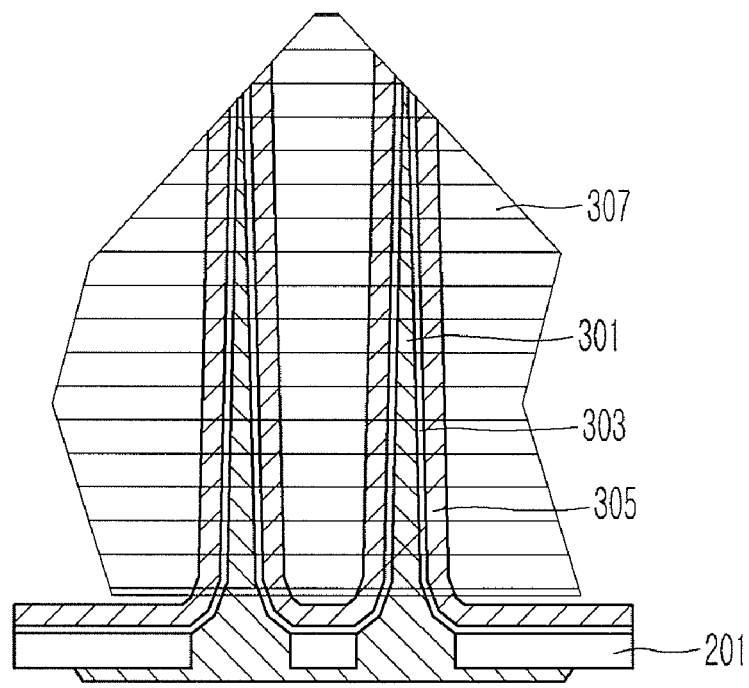
Figure 2M:
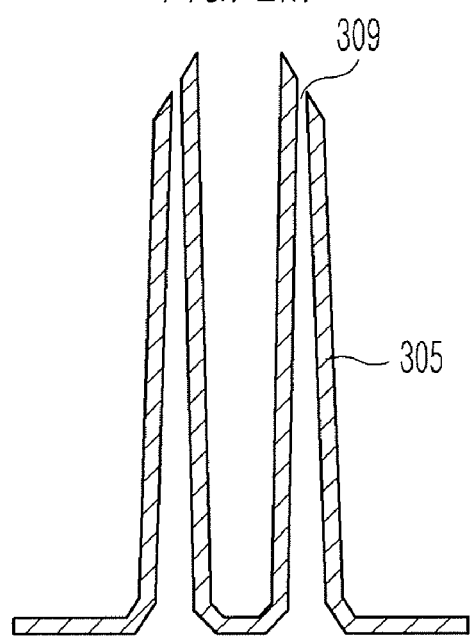
Figure 3A:
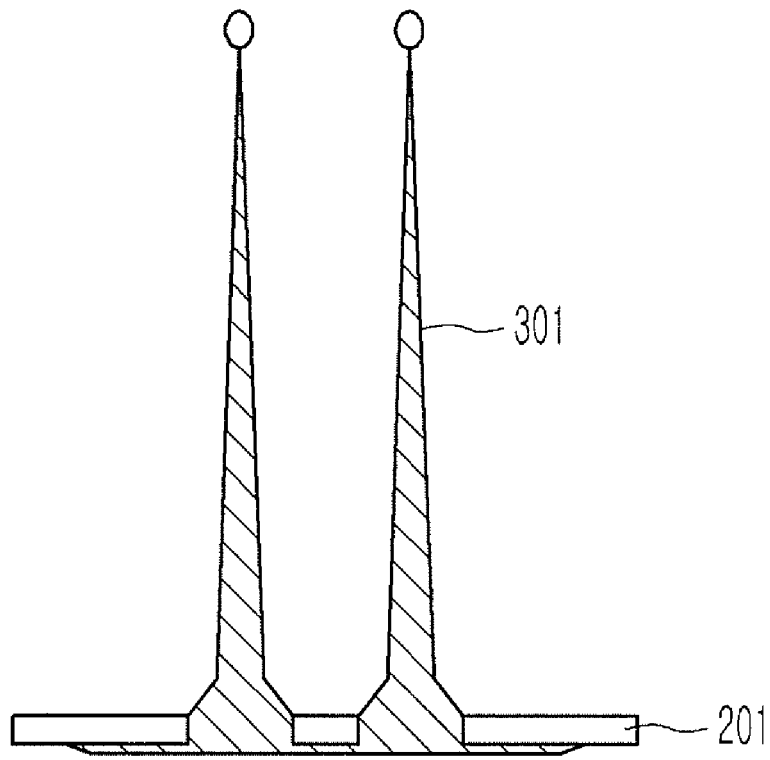
FIGS. 3A and 3B are diagrams showing the arrangement of the resultant structure of FIG. 2H.
Figure 3B:
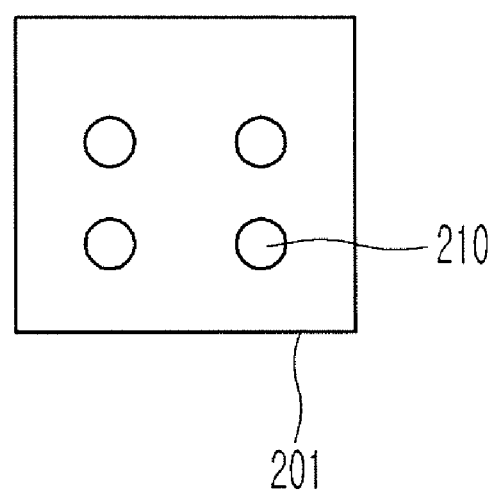
Figure 4A:
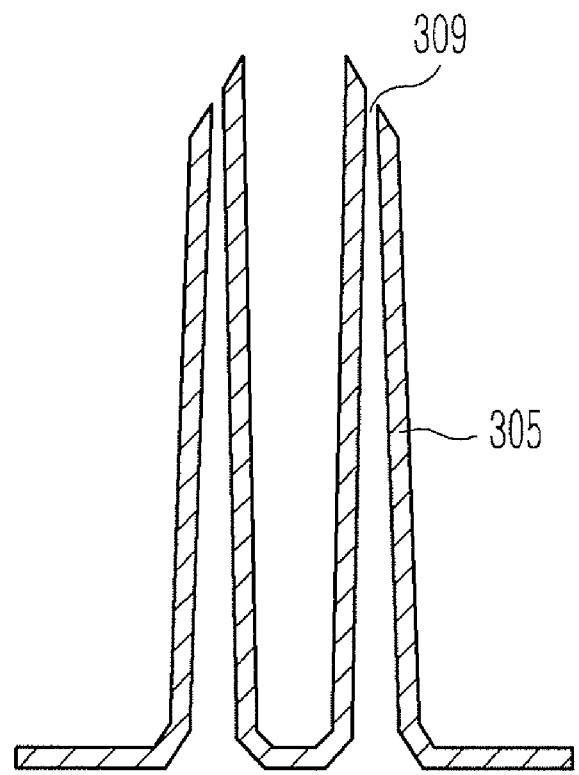
FIGS. 4A and 4B are diagrams showing the arrangement of the resultant structure of FIG. 2M.
Figure 4B:
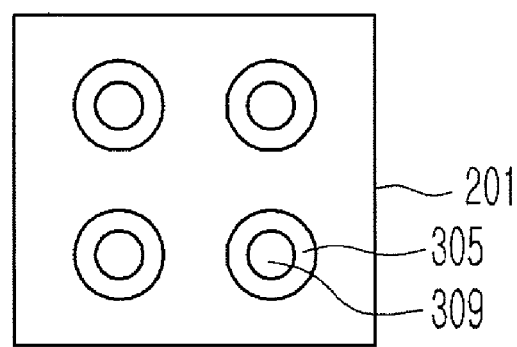

FIGS. 2A through 2M are cross-sectional views illustrating a method of manufacturing the microneedle structure of FIG. 1, FIGS. 3A and 3B are diagrams showing the arrangement of the resultant structure of FIG. 2H, and FIGS. 4A and 4B are diagrams showing the arrangement of the resultant structure of FIG. 2M.

Referring to FIG. 2A, an etch stop layer 202 may be formed on a substrate 201, and a photoresist layer 203 may be formed on the etch stop layer 202.

The substrate 201 may be a solid substrate, such as a silicon substrate.

The etch stop layer 202 may be formed by depositing a silicon oxide layer or a silicon nitride layer using a low-pressure chemical vapor deposition (LPCVD) technique.

Referring to FIG. 2B, an exposure process and a developing process may be performed using a photo mask 204, thereby forming a photoresist (203) pattern as shown in FIG. 2C.

Thereafter, a dry etching process or a wet etching process may be performed using the photoresist (203) pattern as a mask, thereby forming through holes 210 in the substrate 201 as shown in FIGS. 2D and 2E.

Each of the through holes 210 may have a diameter of about 20 to 150 μm. Referring to FIGS. 2D and 2E, formation of the through holes 210 may include patterning the etch stop layer 202 using the photoresist (203) pattern as a mask, etching the substrate 201 using an etch stop (202) pattern as a mask, and removing the remaining etch stop (202) pattern. Alternatively, formation of the through holes 210 may include simultaneously patterning the etch stop layer 202 and the substrate 201 using the photoresist (203) pattern as a mask and removing the remaining etch stop (202) pattern.

Referring to FIG. 2F, a polymer mold 206 may be formed using the substrate 201 having the through holes 210.

The polymer mold 206 may have a predetermined inner space. In this case, the substrate 201 having the through holes 210 may form a bottom surface of the polymer mold 206, while a mechanism capable of moving up and down may form a top surface thereof.

The inner space of the polymer mold 206 may be filled with a photoresist 300. In this case, the photoresist 300 should be viscous and curable by ultraviolet (UV) rays and heat irrespective of the kind thereof. Also, after a metal plating process, the photoresist 300 should be capable of being removed using an etchant.

When the mechanism formed on the top surface of the polymer mold 206 is moved downward by applying pressure, the filled photoresist 300 may be extruded through the through holes 210 of the substrate 201 that forms the bottom surface of the polymer mold 206, and flow out in thin, long shapes.

In this case, an initial diameter of the resultant shape may depend on the diameter of the through hole 210, and a length thereof may depend on a function of viscosity, time, and pressure. That is, a photoresist structure 301 having an appropriate length of about 1 to 5 mm, may be formed under appropriate pressure conditions. The photoresist structure 301 may be cured using a UV light source, heat, or a chemical material.

Referring to FIG. 2H, when the substrate 201 having the cured photoresist structure 301 is separated from the polymer mold 206, the photoresist structure 301 having a desired shape of an appropriate length may be completed.

Referring to FIGS. 3A and 3B, the completed photoresist structure 301 may have needles in a predetermined number equal to the through holes 210 formed in the substrate 201. For example, when 2×2 through holes 210 are formed in the substrate 201, the photoresist structure 301 may have 2×2 needles with thin, long sectional shapes.

Referring to FIG. 2I, a seed layer 303 may be formed on the cured photoresist structure 301.

The seed layer 303 may be formed by depositing a metal material, such as titanium (Ti) or chrome (Cr), using any possible vacuum evaporation method, such as an electronic beam (e-beam) evaporation process, a sputtering process, a CVD process, or an atomic layer deposition (ALD) process. In this case, a region where a hollow will be formed may be coated with a material, such as a photoresist, and then cured using heat or UV rays.

Referring to FIG. 2J, the seed layer 303 may be electroplated with a metal, such as nickel (Ni) or gold (Au), thereby forming a plated layer 305. In this case, the thickness of the plated layer 305 may be variously determined according to the hardness of a needle by controlling temperature, current density, and plating speed. For example, the plated layer 305 may be formed to a thickness of about 5 to 200 μm.

In this case, inclination may be formed to increase the sectional area of a contact portion (or opening) between each of the needles and a biomaterial.

Specifically, referring to FIG. 2K, a wax layer 307 may be formed to cover up to an end tip of the photoresist structure 301 having the plated layer 305. Referring to FIG. 2L, a cutting or sawing process may be carried out. In this case, the wax layer 307 may be formed using an organic or inorganic slurry and cut using a polishing process.

As a result, an inclined opening may be easily formed in an end tip of the needle without breaking or bending the needle. In this case, the opening may have an inclination of about 20 to 80 degrees. According to another exemplary embodiment, a conventional laser cutting process or mechanical cutting process may be performed without a slurry filling process.

By inclining the opening, the effective area of the opening may be increased so that the amount of a biomaterial collected can be increased.

Finally, referring to FIG. 2M, the photoresist structure 301 and the wax layer 307 may be simultaneously removed using a chemical solvent, an ashing process, or a physical process, thereby manufacturing a microneedle having a hollow 309.

Referring to FIGS. 4A and 4B, a 2×2 microneedle structure formed on a substrate 201 having 2×2 through holes 210 may include four microneedles formed along the respective through holes 210. A sectional area of each of the microneedles may have a thin, long hollow 309, and an end tip of each of the microneedles may be inclined.

Meanwhile, a chemical treatment using an anticoagulant, such as EDTA or heparin, may be performed on the through hole 210 of the microneedle having the hollow 309 such that a biomaterial, such as blood is not cured. Alternatively, the through hole 210 of the microneedle having the hollow 309 may be reformed using a plasma treatment such that the through hole 210 has a hydrophilic surface. Furthermore, a biofriendly lubricant may be further applied to facilitate penetration of the microneedle through the skin.

When the microneedle is formed using the photoresist 300 extruded through the through hole 210 of the substrate 201, the diameter of the hollow 309 of the microneedle may be variously determined according to the diameter of the through hole 210, so that the manufacture of the microneedle can be facilitated.

Hereinafter, another method of manufacturing the microneedle structure of FIG. 1 will be described with reference to FIGS. 5A through 5I.

In order to manufacture a microneedle structure according to the present exemplary embodiment, referring to FIGS. 5A through 5F, a through hole 210 may be formed in a substrate 201 having an etch stop layer 202 and a photoresist layer 203, and the substrate 201 may be combined with a polymer mold 206 such that the substrate 201 forms a bottom surface of the polymer mold 206. An inner region of the polymer mold 206 may be filled with a photoresist 300, and pressure may be applied downward to a mechanism formed on a top surface of the polymer mold 206, thereby extruding the filled photoresist 300 from the polymer mold 206.

Figure 5A:
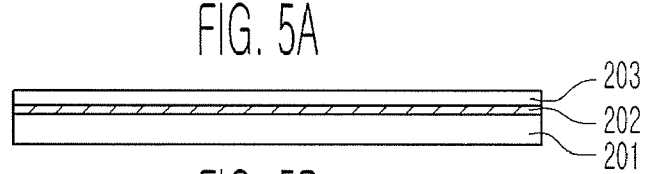
FIGS. 5A through 5I are cross-sectional views illustrating another method of manufacturing the microneedle structure of FIG. 1.
Figure 5B:
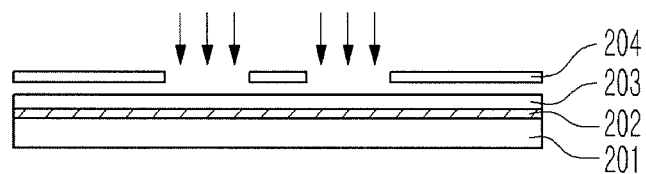
Figure 5C:
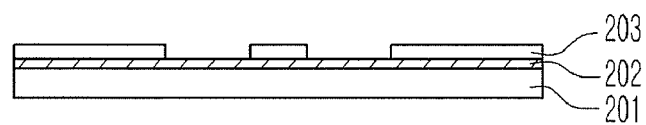
Figure 5D:
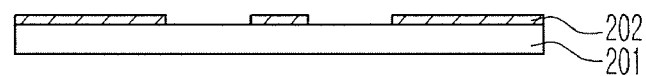
Figure 5E:
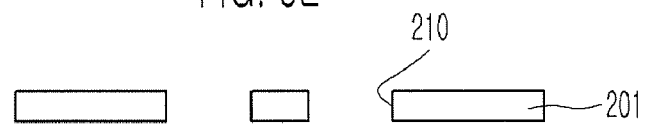
Figure 5F:
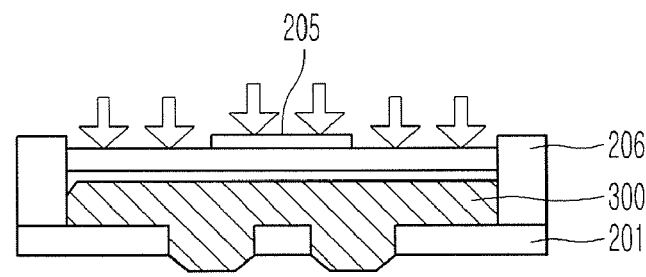
Figure 5G:
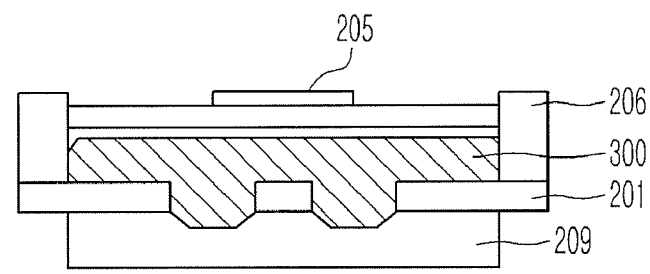
Figure 5H:
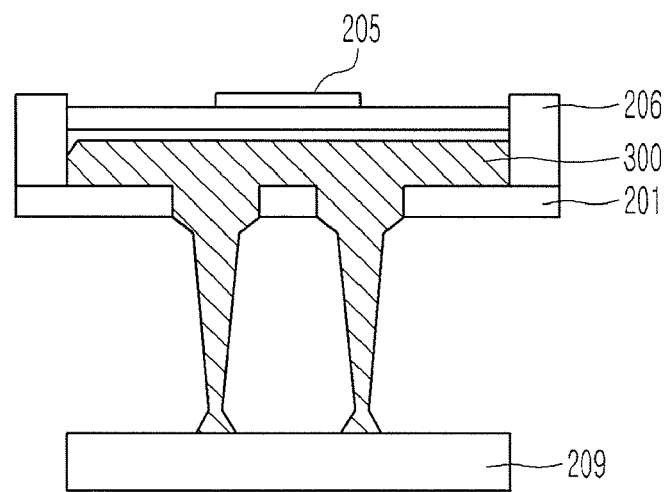

Referring to FIG. 5G, a planar subsidiary substrate 209 may be physically brought into contact with the photoresist 300 flowing out through the through hole 210 so that the extruded photoresist 300 can have a lengthwise needle shape. According to the present exemplary embodiment, it may be easier to appropriately control process conditions applied to the photoresist 300, such as extrusion pressure, extrusion speed, and temperature, according to the shape of a microneedle.

In this case, the subsidiary substrate 209 may be a planar transparent substrate.

Figure 5I:
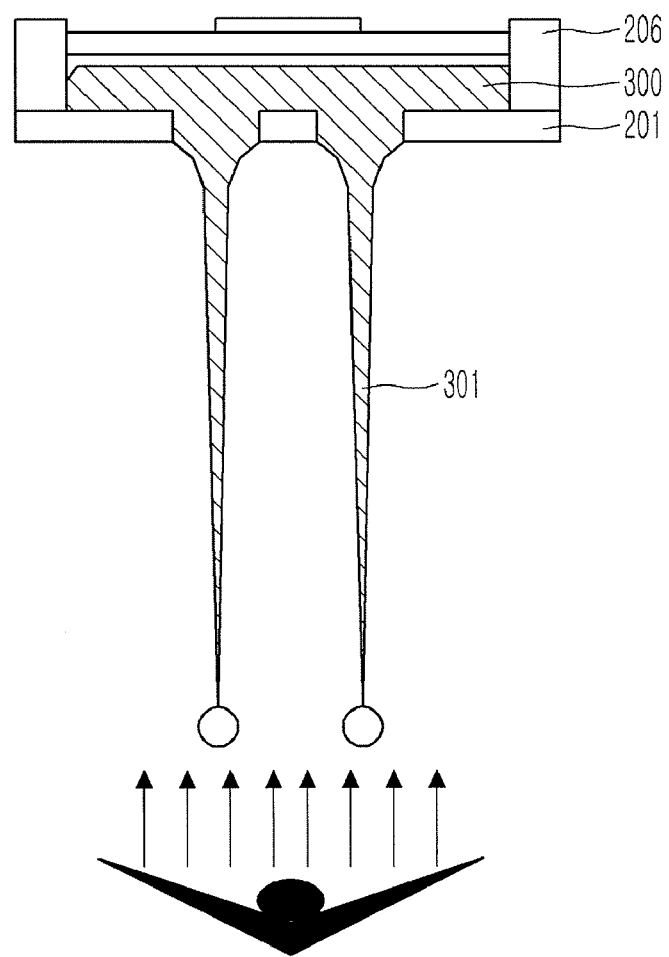

After a needle-type photoresist structure 301 is completed, the photoresist structure 301 may be solidified as shown in FIG. 5I, and subsequent processes may be performed in the same manner as described with reference to FIGS. 2H through 2M.

FIG. 6 is a construction diagram of an application example of the microneedle structure of FIG. 1.

Referring to FIG. 6, a hollow microneedle structure 410 may be typically mounted on an injector. Specifically, a typical injector may include an injector main body 400 and a piston 420. The hollow microneedle structure 410 according to the exemplary embodiment of the present invention may be assembled on top of the injector main body 400 so that a biomaterial can be collected or a medicine may be injected.

According to the exemplary embodiments of the present invention, a hollow microneedle structure can be manufactured to have such a diameter, length, hardness, and inclination angle as to minimize pain. Thus, the hollow microneedle structure may be combined with an apparatus for detecting a biomaterial or injecting cosmetic substances or medicine, and variously applied.

In the drawings and specification, there have been disclosed typical exemplary embodiments of the invention and, although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

What is claimed is:

1. A method of manufacturing a microneedle structure, comprising:
    forming an injection mold having a through hole;
    filling the injection mold with a photoresist formed of a viscous material, and extruding the photoresist from the injection mold through the through hole;
    solidifying the extruded photoresist to form a needle-type photoresist structure;
    forming a seed layer on the surface of the photoresist structure;
    forming a metal plated layer on the seed layer;
    inclining an end tip of the photoresist structure having the metal plated layer; and
    removing the photoresist from the metal plated layer to form a hollow.

2. The method of claim 1, further comprising bringing a subsidiary substrate into contact with the extruded photoresist such that the photoresist has a pillar-type needle shape.

3. The method of claim 1, wherein the microneedle structure has an outer diameter of about 40 to 200 µm and an inner diameter of about 10 to 150 µm.

4. The method of claim 3, wherein inclining the end tip of the photoresist structure having the metal plated layer comprises:
    coating the metal plated layer with a slurry;
    cutting the metal plated layer at a predetermined inclination angle to increase an effective sectional area; and
    removing the slurry.

5. The method of claim 4, wherein the slurry is removed during the removal of the photoresist from the metal plated layer.

6. The method of claim 4, wherein the inclination angle ranges from about 20 to 80 degrees.

7. The method of claim 3, wherein the microneedle structure has an effective length of about 0.5 to 5 mm.

8. The method of claim 1, wherein forming the injection mold having the through hole comprises:
    forming a photoresist layer on a substrate;
    exposing and developing the photoresist layer to form a mask;
    forming a predetermined number of through holes in the substrate according to the type of the mask; and
    assembling the substrate to form a bottom surface of the injection mold.

9. The method of claim 6, further comprising chemically treating the through hole to prevent hardening of a biomaterial.

* * * * *